United States Patent
Hasse et al.

(10) Patent No.: US 9,066,810 B2
(45) Date of Patent: Jun. 30, 2015

(54) COMPLIANT IMPLANT (75) Inventors: Alexander Hasse, Radebeul (DE);
Lucio Flavio Campanile, Schwerzenbach (CH); Tom Overes, Langendorf (CH); Cyril Voisard, Langendorf (CH); Eva Maria Wyss, Tergerfelden (CH)

(73) Assignee: DePuy Synthes Products, Inc., Raynham, MA (US)

( * ) Notice: Subject to any disclaimer, the term of this patent is extended or adjusted under 35 U.S.C. 154(b) by 221 days.

(21) Appl. No.: 13/213,121

(22) Filed: Aug. 19, 2011

(65) Prior Publication Data
US 2012/0078313 A1 Mar. 29, 2012

Related U.S. Application Data (60) Provisional application No. 61/384,399, filed on Sep. 20, 2010.

(51) Int. Cl.
A61F 2/44 (2006.01)

(52) U.S. Cl.
CPC ........... *A61F 2/442* (2013.01); *A61F 2002/443* (2013.01); *A61F 2/44* (2013.01); *A61F 2002/445* (2013.01); *A61F 2/4425* (2013.01); *A61F 2002/449* (2013.01); *A61F 2310/00023* (2013.01)

(58) Field of Classification Search
USPC .............................................. 623/17.11–17.16
See application file for complete search history.

(56) References Cited

U.S. PATENT DOCUMENTS

| | | | | |
|---|---|---|---|---|
| 6,610,093 | B1* | 8/2003 | Pisharodi | 623/17.15 |
| 6,726,720 | B2* | 4/2004 | Ross et al. | 623/17.13 |
| 6,802,867 | B2* | 10/2004 | Manasas et al. | 623/23.5 |
| 7,887,592 | B2* | 2/2011 | Koske | 623/17.15 |
| 2005/0209694 | A1* | 9/2005 | Loeb | 623/17.11 |
| 2007/0010826 | A1 | 1/2007 | Rhoda et al. | |
| 2007/0077267 | A1* | 4/2007 | Molz et al. | 424/423 |
| 2008/0167686 | A1 | 7/2008 | Trieu et al. | |
| 2008/0195206 | A1 | 8/2008 | Chee et al. | |

FOREIGN PATENT DOCUMENTS

| | | |
|---|---|---|
| CN | 1870952 A | 11/2006 |
| EP | 0716841 | 6/1996 |
| FR | 2723841 | 3/1996 |
| FR | 2921820 | 4/2009 |
| WO | WO 00/23014 | 4/2000 |
| WO | WO 2005/011522 A2 | 2/2005 |
| WO | WO 2005/039454 | 5/2005 |
| WO | WO 2007/075411 | 7/2007 |
| WO | WO 2007/095333 | 8/2007 |
| WO | WO 2008/022206 | 2/2008 |

OTHER PUBLICATIONS

International Patent Application No. PCT/US2011/048343: International Search Report dated Nov. 4, 2011, 9 pages.

* cited by examiner

*Primary Examiner* — Nicholas Woodall
(74) *Attorney, Agent, or Firm* — Baker & Hostetler LLP

(57) ABSTRACT

An implant extends along a central axis, and includes first and second members spaced along the central axis. The implant can include a compliant interface. The compliant interface includes a plurality of spring members, the plurality of spring members arranged to space apart the first member from the second member along the central axis.

35 Claims, 5 Drawing Sheets

COMPLIANT IMPLANT

CROSS-REFERENCE TO RELATED APPLICATIONS

This claims the benefit of U.S. patent application Ser. No. 61/384,399 filed on Sep. 20, 2010, the disclosure of which is hereby incorporated by reference as if set forth in its entirety herein.

TECHNICAL FIELD

The present disclosure generally relates to an orthopedic implant, and in particular relates to a compliant orthopedic implant.

BACKGROUND

The motion pattern of a healthy joint is complex and involves rotation and translations, sometimes alone and sometimes in combination. Accordingly, the instantaneous center or axis of rotation moves along with the joint. Typical conventional arthoplasty implants are typically limited in their ability to realize complex motions that would better replicate the physiological motion of the intact anatomical structures, and thus do not respond accurately to anatomical loads.

For example, conventional ball-on-socket articulations are limited to rotations, provide only a limited amount of lateral translation and no axial damping. Moreover, such implants tend to generate wear particles that can cause osteolysis in the neighbouring bony structures or induce immune response in case of toxic materials. So-called artificial discs based on a soft core between two rigid plates provide more motion, however the long term stability of the involved polymers is still not well understood. Still other implants have been found to rotate, translate, or undergo other undesirable motion, for instance when placed under compression.

SUMMARY

In accordance with one embodiment, an orthopaedic implant is compressible along a central axis. The orthopaedic implant includes a first member, a second member, and a compliant interface that is connected between the first and second members. The compliant interface includes at least a pair of spring members that are bracingly connected. The spring members space the first member from the second member along the central axis.

DESCRIPTION OF THE DRAWINGS

The foregoing summary, as well as the following detailed description of the various embodiments of the application, will be better understood when read in conjunction with the appended drawings. For the purposes of illustrating the various embodiments of the disclosure, reference is made to the drawings. It should be understood, however, that the application is not limited to the precise arrangements and instrumentalities illustrated in the drawings, in which.

DETAILED DESCRIPTION

Figure 1:
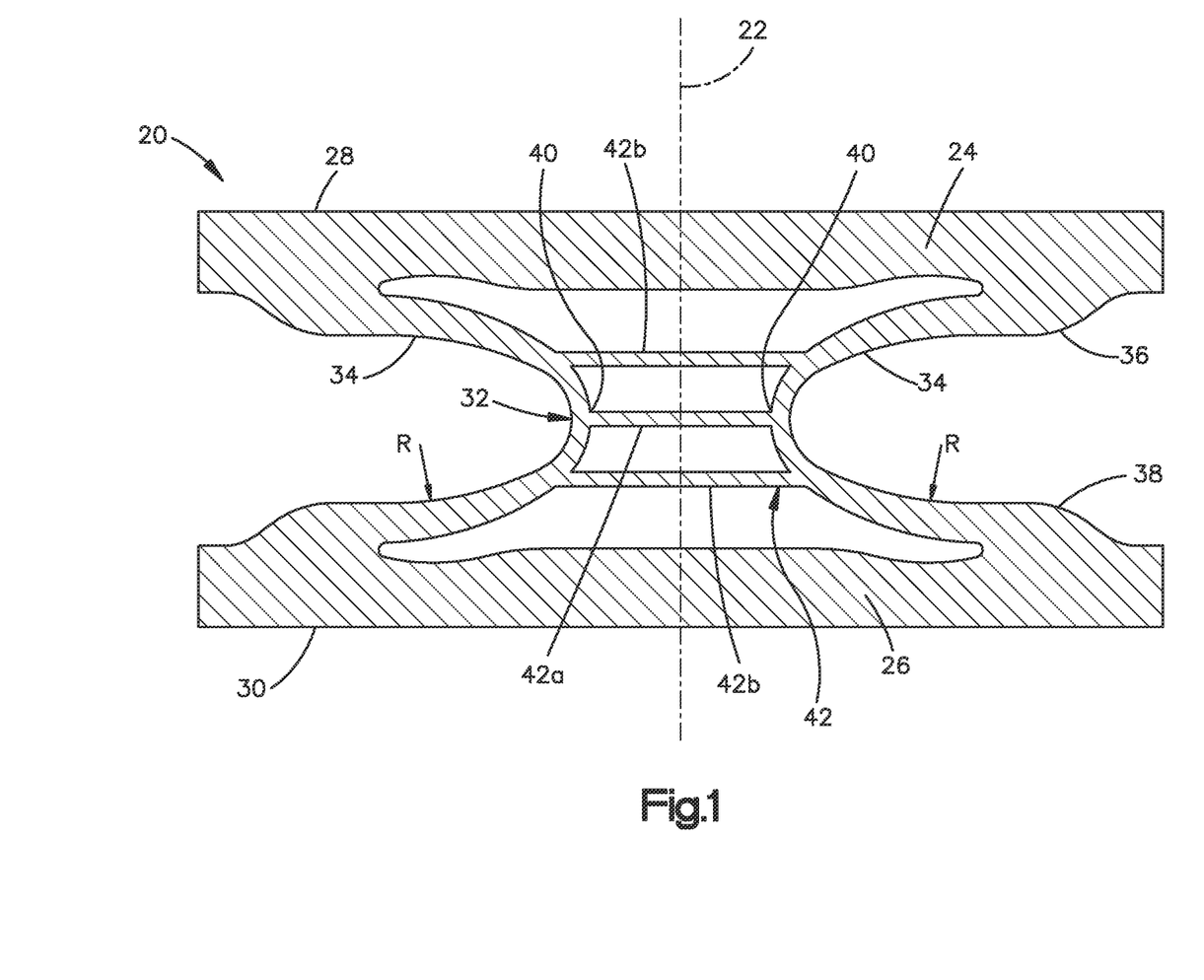
FIG. 1 is a sectional side elevation view of an orthopedic implant constructed in accordance with one embodiment, wherein the section of FIG. 1 is taken along line 1-1 of FIG. 2.
Figure 2:
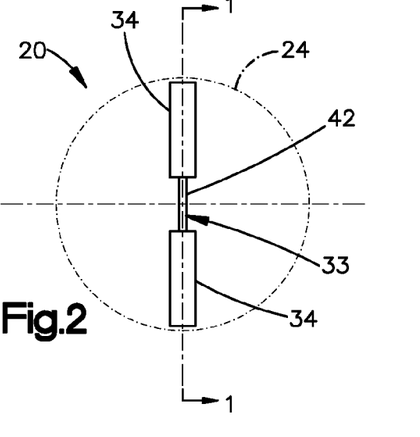
FIG. 2 is a schematic top view of the orthopaedic implant illustrated in FIG. 1.

Referring to FIGS. 1-2, a compliant orthopedic implant 20 can be configured as an intervertebral disc implant that can replace a natural intervertebral disc in the lumbar or cervical section of the spinal column, or at any alternative location in the spinal column as desired, or can be configured as any artificial joint as desired, such as a finger joint, a hip joint, elbow joint, shoulder joint, wrist joint, knee joint, or the like. The implant 20 extends vertically along a central axis 22, and includes a first member such as a first end member 24 configured to abut a first adjacent bone, a second member such as a second end member 26 that is vertically spaced from the first end member 24 along the central axis 22 and is configured to abut a second adjacent bone, and a compliant intermediate interface 32 that is coupled between, and can be connected to, the first and second end members 24 and 26, which can be configured to rotate about the central axis 22, such that the central axis 22 can define an axis of rotation for the first and second end members 24 and 26. For instance, one or both of the first and second end members 24 and 26 can rotate relative to the other end member about the central axis 22 of the orthopedic implant 20.

The first end member 24 can be a rigid plate, such as an endplate that can be sized and shaped as desired. The first end member 24 can define a bone engagement surface 28 that can be flat or otherwise shaped so as to contact a neighbouring first bone structure, e.g. a first vertebral body. The second end member 26 can be a rigid plate, such as an endplate that can be sized and shaped as desired. The second end member 26 can define a bone engagement surface 30 that can be flat or otherwise shaped so as to contact a neighbouring first bone structure, e.g. a first vertebral body. The second end member 26 is illustrated as an inferior end member, while the first end member 24 is illustrated as a superior end member, though the implant 20 can be oriented as desired during use. The compliant intermediate interface 32 can extend along a central axis that coincides with or is parallel to the central axis 22 of the orthopedic implant 20. In one embodiment, the compliant intermediate interface 32 is symmetrical about its central axis. The compliant intermediate interface 32 is configured to provide both a desired level of stiffness to the implant 20 that resists compression and extension along the central axis 22, but at the same time allows a desired amount of deformation of the implant 20 against the stiffness of the interface 32, such as vertical compression and pivoting about an axis that intersects the central axis 22, and can be substantially perpendicular to the central axis 22. The compliant intermediate interface 32 also have a stiffness that provides a spring force that resists rotation of one or both end members 24 and 26 about the central axis 22, but at the same time allows the first and second end members 24 and 26 to rotate about the central axis 22 against the spring force of the intermediate interface 32.

Figure 3:
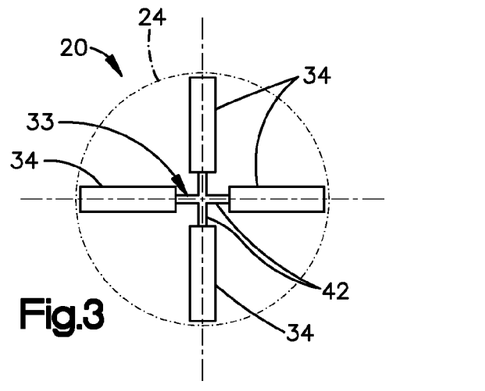
FIG. 3 is a schematic top view of an orthopedic implant similar to the orthopedic implant illustrated in FIG. 1, but including two pair of perpendicularly oriented spring members that intersect.

The implant 20 is illustrated as a one-piece integral structure, though it should be appreciated that the various components of the implant 20 can be discreetly connected to each other as desired. The intermediate compliant interface 32 is arranged between the first and second end members 24 and 26, and includes at least one spring member 34, for instance at least a pair of spring members, that are arranged to space apart the first and second end members 24 and 26. The spring members 34 can be concave in accordance with one embodiment, such as C-shaped leaf springs as desired. Each of the spring members 34 can define a first end or base 36 which is connected to the first end member 24, and an opposed second end or base 38 which is connected to the second end member 26. Each of the spring members 34 defines a substantially C-shaped concave arc that is defined by a radius of curvature R along its length, and further includes a vertex 40 directed towards the central axis 22 of the implant 20. The radius of curvature R can vary along its length, and can be within a range that is greater than approximately 1 mm, for instance greater than 2 mm and less than approximately 20 mm, though the radius of curvature R can define any suitable alternative distance as desired. The springs 34 are configured such that the radius of curvature R is at its minimum in the vertices 40, though it should be appreciated that the minimum radius of curvature R can be disposed anywhere along the length of the spring member 34 as desired. Further, the spring members 34 are spaced apart from each other and extend along respective vertical planes, at least some of which can be substantially co-planar with the planes of one or more, up to all, of the other spring members 34 as illustrated in FIG. 2. Furthermore, and at least some up to all of the planes intersect at a common axis that coincides with the central axis 22 as illustrated in FIG. 3.

It is recognized that disc replacement implants, for instance in the lumbar spine, experience large forces during operation, for instance axial compression forces (e.g., along a direction parallel to, for instance coincident with, the central axis) up to 2000 Newtons. The compliant interface 32 further includes a hub 33 that is connected between one or more, up to all, of the spring members 34. The hub 33, and thus the compliant interface 32, can include at least one stiffening member in the form of a bracing 42 that is connected between, and can be connected to, at least a pair of the spring members 34. As illustrated, the bracings 42 extend along a direction that has a directional component that is transverse to the central axis 22. In accordance with one embodiment, the bracings 42 extend in a direction that is substantially transverse to the central axis 22, though the bracings 42 can extend in any direction angularly offset with respect to the central axis 22. The transverse bracings 42 can extend parallel to each other as illustrated, such that the middle one of the three transverse bracings 42 connects the vertices 40 of the two spring members 34. The transverse bracings 42 can be ring-shaped in a cross-section transverse to the central axis 22, can be bar-shaped and can have a cylindrical, prismatic, or any suitable alternative cross-sectional shape as desired. The bracings 42 can have a cross-sectional area that can be within the range of approximately 4 $mm^2$ and approximately 6 $mm^2$. The ring shaped configuration of the one or more bracings 42 is particularly suitable when the compliant interface includes three or more spring members 34.

The first and second end members 24 and 26 can define a rectangular, circular or oval footprint taken from a view parallel to the central axis 22, or can alternatively define any suitably shaped footprint as desired. The end members 24 and 26 can be elongate along a plane that is substantially transverse to the central axis 22. The superior and inferior bone engagement surfaces 28 and 30 can be coated or otherwise treated as desired to promote osseointegration. Preferred coatings are pure titanium or calcium phosphate. Furthermore, the first and second end members 24 and 26 can include various three-dimensional structures (e.g., like teeth, spikes or keels or the like) that extend from the respective bone engagement surfaces 28 and 30 so as to enhance primary fixation.

The compliant interface 32 can include at least one spring member 34, such as a plurality of spring members 34. In accordance with the embodiment illustrated in FIG. 2, the compliant interface 32 includes a pair spring members 34, each circumferentially equidistantly spaced with respect to each other, though it should be appreciated that the spring members 34 can be variably spaced. Furthermore, as will be described in more detail below, the compliant interface 32 can include any number of spring members as desired, arranged and oriented in any manner as desired. In accordance with the illustrated embodiment, each of the spring members 34 can be substantially planar in the vertical direction, and extend along a plane between the first and second end members 24 and 26. For instance, each of the spring members can be elongate along a vertical plane that includes the central axis 22 of the implant 20. Accordingly, each of the corresponding planes defined by the spring members 34 can include the central axis 22. The spring members 34 can be spaced apart from each other as desired. Because the spring members 34 are equidistantly spaced in accordance with the illustrated embodiment, the planes of the spring members 34 are angularly offset equally, or about an angle of approximately 180°. It should thus be appreciated that the compliant interface 32 can include a pair of coplanar spring members 34 that are opposed at an angle of approximately 180°.

In accordance with the illustrated embodiment, the compliant interface 32 includes a plurality of bracings 42 that extend between the spring members 34, and can thus span across the central axis 32, for instance along a direction substantially transverse to the central axis 22. In accordance with one embodiment, one or more first bracings 42 can be connected between the vertices of the spring members 34, and one or more second bracings 42 can be connected to the spring members 34 at locations offset from the vertices. For instance, a first or inner bracing 42a is connected between the vertices 40 of the spring members 34, while a pair of second or outer bracings 42b is connected between the spring members 34 at a location offset with respect to the vertices 40. Thus, it can be said that the compliant interface 32 can include at least a pair of bracingly connected spring members that space the first end member 24 apart from the second end member 27 along the central axis 22. For instance, a second bracing which can be configured as a first outer bracing 42b is connected between the spring members 34 at a location above the vertices 40, and a third bracing which can be configured as a second outer bracing 42b is connected between the spring members 34 at a location below the vertices 40.

Accordingly, as the first and second end members 24 and 26 are compressed relative to each other, for instance along the central axis 22, the vertices are biased to translate toward each other (for instance when the spring members 34 are 180° opposed) which thereby places the first bracings 42a in compression. Furthermore, as the end members 24 and 26 are compressed relative to each other, the locations of the opposed spring members 34 offset from the vertices are biased to translate away from each other, and thereby place the second and third bracings 42b-c in tension. Accordingly, due to the concave shape of the spring members 34, different portions of the intermediate compliant interface 32 can be compressed and flexed in a direction substantially transverse to the central axis 22 so that the stiffness of the compliant intermediate member 32 is significantly enhanced but the orthopaedic implant 20 is still compliant.

Figure 4:
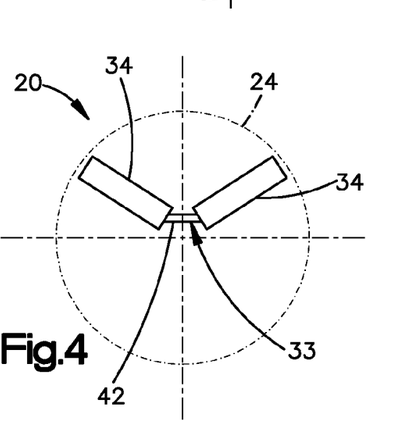
FIG. 4 is a schematic top view of an orthopedic implant similar to the orthopedic implant illustrated in FIG. 1, but, a pair of angularly offset spring members that intersect.

Referring to FIGS. 2-6, it should be appreciated that the spring members 34 and bracings 42 can be constructed, shaped, and oriented in accordance with any suitable alternative embodiment as desired. For instance, FIG. 2 is a schematic top view of the implant 20 illustrated in FIG. 1. In the arrangement as illustrated in FIG. 4, the compliant interface 32 includes two spring members 34 that each extends along a vertical plane. However, unlike the embodiment illustrated in FIG. 1, the planes illustrated in FIG. 4 are not substantially co-planar, and thus define an angle less than 180°, for instance between 90° and 180°, though the angle could be less than 90° if desired. The planes defined by the spring members 34 intersect at a common axis that can coincide with the central axis 22, or can be offset with respect to the central axis 22. Furthermore, the planes defined by opposed spring members 34 can be co-planar, while the planes defined by angularly offset spring members 34 can intersect at the central axis of the orthopaedic implant. Further, the bracings 42 are arranged orthogonal to the median line of the angle defined by the planes of the two spring members 34.

Referring to FIG. 3, each spring member 34 is elongate along a plane that includes the central axis 22 of the implant 20. Accordingly, each of the corresponding four planes defined by the spring members 34 intersects at a common axis that coincides with the central axis 22. Because the four spring members 34 are equidistantly spaced, the four planes are angularly offset equally, or about an angle of approximately 90°. It should thus be appreciated that the spring members 34 and corresponding planes include two pairs of coplanar spring members 34 that are opposed at an angle of approximately 180°.

In accordance with the illustrated embodiment, first and second groups of bracings 42 extend between the first and second opposed pairs of spring members 34. Thus, the bracings 42 of the first group are thus angularly offset (e.g., substantially perpendicular as illustrated) with respect to the bracings 42 of the second group. One or more, up to all, of the bracings 42 of each group can intersect the bracings 42 of the other group, or can alternatively be vertically offset with respect to the bracings 42 of the other group. The bracings 42 that intersect each other can also be integral with each other and can be integral with the spring members 34 which, in turn, can be integral with the first and/or second end members 24 and 26, such that the end members 26 and 26, the bracings 42, and the spring members 34 can be constructed as a unitary integral structure. Alternatively, one or more of the components of the orthopaedic implant 20 can be discretely connected to each other.

In accordance with one embodiment, the compliant intermediate interface 32 can be made from a material that has a modulus of elasticity in the range 10-120 GPa. For instance, the interface can be made from titanium having a modulus of elasticity of approximately 110 GPa, titanium alloys having a modulus of elasticity of approximately 30 GPa, a glass fiber-reinforced composite having a modulus of elasticity of approximately 20 GPa. Alternatively, it should be appreciated that the compliant intermediate interface 32 can be made from a material having any suitable alternative modulus of elasticity as desired. For instance, thermoplasts have a modulus of elasticity of less than approximately 10 GPa, and polyetheretherkeytones have a modulus of elasticity of approximately 4 GPa.

The orthopaedic implant 20 can be made from a metal or metal alloy, e.g. one of the following alloys: Stainless steel 316L, Ti6Al7Nb, Ti6Al4V, Ti15Mo, Ti23Nb2Ta0.7Zr or Zr22Cu8Fe12Al. Alternatively, the implant can be made from a polymer or a reinforced polymer, preferably comprising PEEK or carbon-reinforced PEEK. When the orthopaedic implant 20 is made from a polymer, the polymer of the first and second members can be formed as a polymer matrix with the compliant interface embedded therebetween. The polymer matrix may have the property of reducing bone in-growth into the compliant interface. In accordance with one embodiment, the orthopaedic implant 20 can define a maximum size defined by the length along a first direction substantially transverse to the central axis 22, a width along a second direction that is substantially transverse to both the first direction and the central axis 22, or the height of the implant that extends substantially along the central axis 22. The maximum size can be greater than 8 mm, such as greater than 10 mm, and can be less than 12 cm, such as less than 10 cm.

Figure 5:
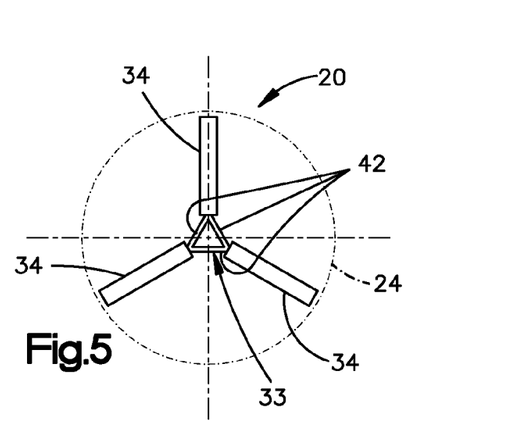
FIG. 5 is a schematic top view of an orthopaedic implant similar to the orthopaedic implant illustrated in FIG. 1, but including three spring members that are equidistantly angularly displaced and intersect.
Figure 6:
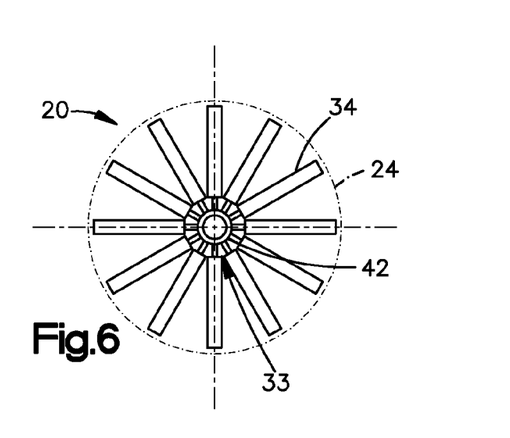
FIG. 6 is a schematic top view of an orthopaedic implant similar to the orthopaedic implant illustrated in FIG. 1, but including a plurality of spring members that are equidistantly angularly displaced and intersect.

In the arrangement illustrated in FIG. 5, the compliant interface 32 includes three spring members 34 that are equidistantly angularly displaced at 120° relative to each other. Thus, each of the spring members 34 is elongate along a respective vertical plane, such that all of the planes intersect at a common axis that coincides with the central axis 22. Further, the hub 33 defines a triangle, which can be equilateral, each side of which is defined by a group of transverse bracings 42. Thus, the vertices or corners of the equilateral triangle can each be connected to one of the spring members 34. The center of the equilateral triangle defined by the hub 33 can lie on the central axis 22.

It should be appreciated that the compliant interface 32 can include any number of spring members 34 as desired, either equidistantly or variably spaced. For instance, referring to FIG. 6, the compliant interface 34 includes twelve spring members 34 that extend along angularly equidistantly displaced planes, respectively, such that the twelve planes are arranged at an angle of 30° relative to each other. Thus, the twelve spring members 34 are organized as six pairs of spring members 34, such that a corresponding six groups of at least one bracing 42 can be respectively connected between the six pairs of spring members 34. The bracings 42 extend parallel to and between the respective spring members 34 to which the bracings 42 are attached, and can integrally or discretely intersect at the central axis 22. Accordingly, the hub 33 can assume any regular or irregular polygonal shape that more closely approximates the shape of a circle as the compliant interface 32 includes increasing numbers of spring members 34. The hub 33 can include spokes defined by the bracings 42 that can intersect the central axis 22.

It should be further appreciated that the compliant interface 32 can be constructed having fewer groups of bracings 42 than pairs of spring members 34, such that at least one of the spring members 34 up to all of the spring members 34 can be connected by a group of at least one bracing 42, and at least one of the spring members 34 up to all of the spring members 34 can be devoid of attachment to any other spring member 34 via any bracings. Thus, the compliant interface 32 can include any number of spring elements 34 arranged in any desired manner, and any corresponding number of bracings 42 connected between the spring elements 34.

Figure 7A:
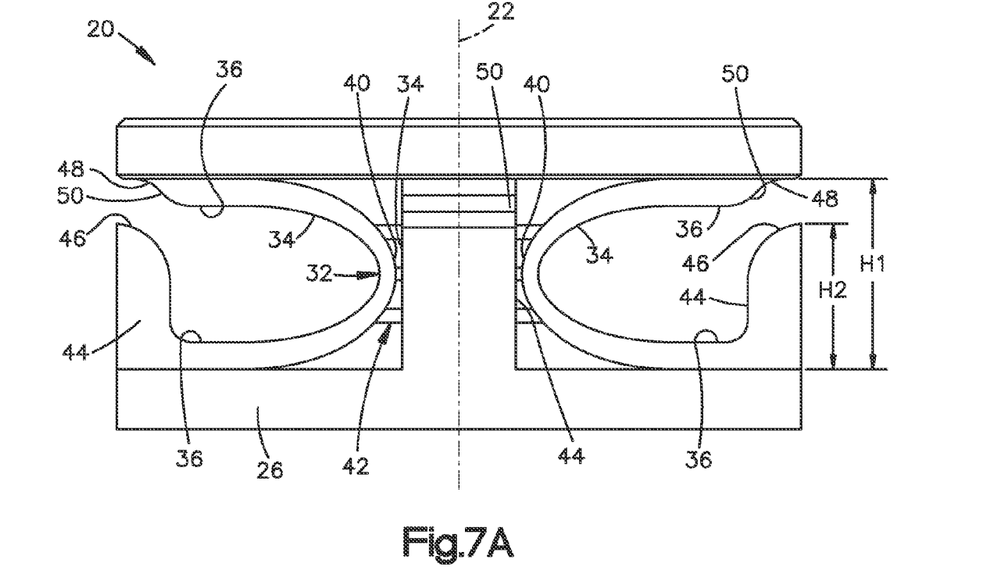
FIG. 7A is a first side elevation view of an orthopedic implant illustrated in FIG. 3, but constructed in accordance with an alternative embodiment, including two pair of opposed spring members and corresponding compression stop members.
Figure 7B:
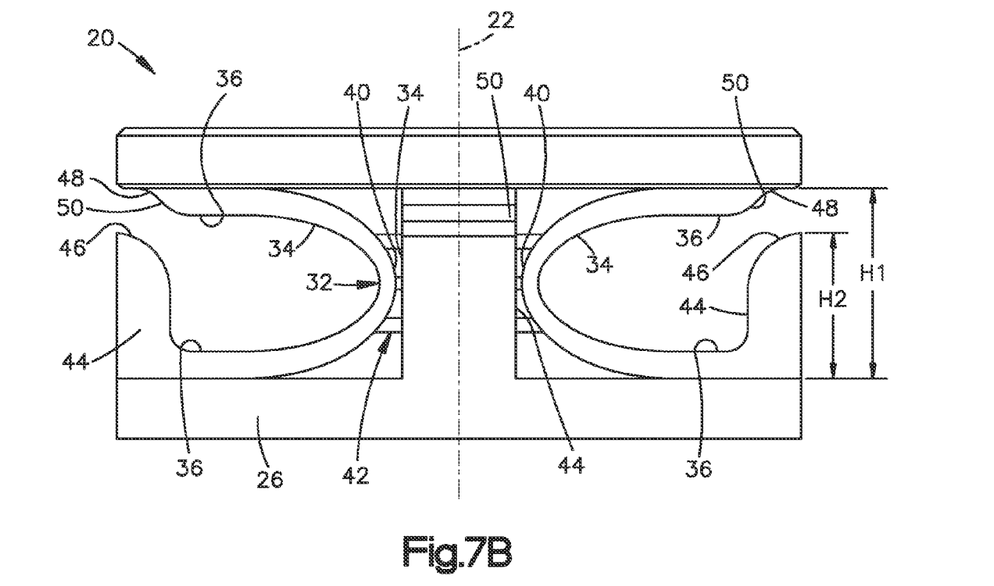
FIG. 7B is a second side elevation view of the orthopedic implant illustrated in FIG. 7A, taken orthogonal with respect to the side elevation view illustrated in FIG. 7A.

Referring now to FIGS. 7A-B, the implant 20 can include four spring members 34 as described above with respect to FIG. 3. Furthermore, the compliant interface 32 can include at least one stop member 44 that is configured to limit the amount of compression of the first and second end members 24 and 26 relative to each other along the central axis and/or pivotal movement of the end members 24 and 26 about an axis which can be coincident with or offset from the central axis 22. In accordance with the illustrated embodiment, one or more up to all spring members 34 can each include a stop member 44. Each stop member 44 can extend from the inferior base 36 of the spring member 34 along a vertical direction substantially parallel to the central axis 22 toward the superior base 36 and end member 24, or can extend from the end member 26 at a location spaced from the base 36 of the spring member 34. Thus, it can be said that the stop members 44 are supported by the end member 26. It should be further appreciated that each stop member 44 can extend along a direction from the superior end member 24 toward the inferior end member 26.

The stop members 44 are illustrated as posts that can be integral with one or both of the corresponding end member 26 and spring member 34 at their proximal end, and define respective contact surface in the form of a stop surface 46 at their distal ends that are spaced from the opposed end member 24 during normal operation. In accordance with the illustrated embodiment, the stop members 44 are connected to the second end member 26 and extend toward the first end member 24. The stop members 44 define a height H2 which is less than the height H1 of the compliant interface 32 when the spring members 34 are in their respective neutral positions. Accordingly, the stop surfaces 46 are spaced from the superior end member 24. Further, the stop members 44 can be disposed adjacent the laterally outer ends or periphery of the spring members 34, or at the mouth of the open portion defined by the concavity of the spring members 34. Alternatively, the stop surface 46 can extend from the end member 26 at a location spaced from the spring member 34. It should be appreciated that the stop members 44 can be provided alone or in combination with the spring members 34 at their bases that connect to the contact members. One or more of the stop members 44 can also be provided by one or more of the spring members 34. For instance, one or more up to all of the spring members 34 can include a stop member 44 that extends along a direction from one of the end members toward the other end member. The stop member 44 or stop members 44 can thus extend along a direction that is substantially parallel to the central axis 22 of the orthopedic implant 20.

The orthopedic implant 20 can further define a seat 48 that is configured to receive and abut the stop surface 46 when the corresponding spring member 34 has compressed from its neutral position to a maximum amount of permissible compression along the central axis 22. It should be appreciated that the spring members 34 can compress from their neutral positions in response to a compressive force, or in response to pivotal movement of the end members 22 and 24 about a pivot axis that is angularly offset (such as perpendicular) with respect to the central axis 22. In accordance with the illustrated embodiment, the seat 48 can be provided as a contact member, such as a curved contact surface 50 defined by the base 36 of the spring member 34 that is opposite the base 36 or end member 26 that supports the proximal end of the stop member 44. The contact surface 50 can be concave, and the corresponding stop surface 46 can be convex and thus shaped to contact and nest in the contact surface 50.

The stop surface 46 and contact surface 50 can taper, for instance curvedly, along a direction parallel to the central axis 22, such that the contact surface 50 can slide on the stop surface 46 along a direction angularly offset with respect to the central axis 22. Accordingly, when one side of the compliant interface 32 is compressed as far as the height H2 of the stop member 44, the stop surfaces 46 end members 24 and 26 can laterally translate relative to each other, an/or pivot about a pivot axis that is angularly offset with respect to the central axis 22 upon a coaxial compression of the implant 20. Furthermore, depending on the construction and rigidity of the spring members 34, that end members 24 and 26 can rotate about the central axis 22. If the entire implant 20 is fully compressed, the engagement of the contact surfaces 46 and 50 about the implant 20 prevents further compression, lateral translation, and pivotal motion.

Under standard physiological mechanical loads, the stop surfaces 46 and the corresponding contact surfaces 50 are not configured to abut each other, thereby significantly reducing or eliminating wear surfaces compared to conventional implants that include surfaces that contact each other and move relative to each other during normal operation. Thus, the orthopedic implant 20 can be a one-piece integral structure, such that a monolith version of an arthroplasty implant reduces or eliminates wear sources compared to certain conventional implants, as moving surfaces of the orthopedic implant do not come into contact with each other during normal operation. Furthermore, the compression stiffness of the orthopedic implant 20 can be decoupled with respect to the pivotal stiffness of the orthopedic implant 20 and rotational stiffness of the orthopedic implant 20. It should be appreciated that the stiffness of orthopaedic the implant 20 can be tuned as desired, for instance by varying the stiffness of one or more, up to all, of the spring members 34 and/or one or more, up to all, of the bracings 42.

Even when the stop surfaces 46 and the contact surfaces 50 abut each other, the end members 24 and 26 can be capable of rotating relative to each other about the central axis 22 of the orthopedic implant 20. Furthermore, if the orthopedic implant 20 is pivoted such that one or more less than all of the corresponding stop surfaces 46 and contact surfaces 50 abut (for instance on one side of the orthopaedic implant 20), the other side of the orthopaedic implant 20 can be further compressed, thereby pivoting the implant, until the corresponding contact surfaces abut. Furthermore, the end members 24 and 26 can translate laterally with respect to each other until the corresponding stop surfaces 46 and contact surfaces 50 of the other side of the orthopaedic implant 20 abut.

In accordance with the implant 20 illustrated in FIGS. 1, 3, and 7A-B, the bracings 42 can be configured to selectively increase both the stiffness as well as the strength of the intermediate compliant interface 32 when symmetrically loaded (for instance a compressive axial load) along a direction substantially parallel or coincident with the central axis 22, while at the same time not significantly adding to the stiffness of the compliant interface 32 with respect to pivotal motion of the end members 24 and 26 about a pivot axis that is angularly offset with respect to the central axis 22 (e.g., flexion or lateral motion) or axial rotation of the end members 24 and 26 about the central axis 22. For instance, when the orthopedic implant 20 is symmetrically loaded, for instance under compression, the vertices 40 of the spring members 34 are biased toward each other, which places the middle brace 42 in compression. At the same time, locations of the spring member 34 at locations offset from the vertices are biased away from each other, which places the outer braces in tension. Accordingly, the bracings 42 provide a stiffness that substantially rigidly constrains the spring members 34 at the connection locations with the bracings 42, thereby increasing the stiffness and strength of the compliant interface 32 with respect to compression loads.

When an asymmetric compression load and/or axial rotational load are applied to the implant 20, the bracings 42 operatively join the spring members 34 such that the spring members 34 flex in concert in response to the applied load. In particular, the connection of the bracings 42 between the spring members 34 provide no or negligible resistance to pivotal motion (such that one spring member 34 is compressed while the other spring member 34 is flexed) and axial rotational motion, whereby both spring members 34 that are connected by the bracings 12 are flexed along a common radial direction. Accordingly, the compliant interface 32 reacts to a symmetric load in a different manner with respect to an asymmetric load, such that compression, pivotal motion, and rotational motion are substantially de-coupled.

In the event that a load is placed eccentrically on the compliant interface, the first and second end members 34 and 36 of the orthopedic implant can pivot about a pivot axis that is movable along a direction that is transverse to the central axis of the implant. Thus, the orthopedic implant 20 can provide a high compression stiffness along its central axis 22 as desired while at the same time allowing pivotal motion along perpendicular transverse axes (e.g., to accommodate lateral bending and flexsion/extension), and rotation about a third axis that is angularly offset, for instance perpendicular, to the central axis 22 (e.g., to accommodate rotation about the central axis of the orthopedic implant). The orthopedic implant 20 can further provide independent stiffnesses that resist pivotal motion, compression, and rotation. The stiffnesses can be decoupled or weakly coupled, and the coupling can be modified by design as desired. The orthopaedic implant 20 can thus be configured to provide different axial, pivotal, rotational, and translational stiffnesses. The orthopaedic implant 20 can be configured smaller and more thin-walled than conventional implants. The orthopaedic implant 20 can be used for instruments as well, providing a simple monolith design suitable for large-scale manufacturing. The orthopaedic implant 20 can be provided with reduced instances of attrition compared to conventional implants.

It should be appreciated that one or both of the first and second end members 24 and 26 can pivot with respect to the other end member about a pivot axis that is transverse to the central axis 22 of the orthopedic implant 20, or includes a directional component that is transverse to the central axis 22 of the orthopedic implant 20. Accordingly, the orthopaedic implant 20 constructed in accordance with one embodiment has the ability to shift the pivot axis, providing simultaneous translation and pivoting. The compliant interface 32 allows the instaneous pivot axis to displace as the end members 24 and 26 pivot relative to each other, thereby allowing translational movement of one or both of the end members 24 and 26 as the end member or end members 24 and 26 pivot. The central axis 22 of the orthopedic implant 20 can extend vertically in an upright patient, such that the pivot axis is transverse to the central axis 22, and thus horizontal in the upright patient. The pivot axis can thus migrate horizontally in an upright patient. For instance, the pivot axis can migrate angularly in a horizontal plane. Thus, the compliant interface 32 can allow the pivot axis to displace along a direction that has a directional component substantially transverse to the central axis 22 of the orthopaedic implant 20.

It should be appreciated that one side one side of the orthopaedic implant 20 can become compressed along a direction substantially parallel to the central axis 22, while another side of the orthopaedic implant 20 can be flexed/extended along a direction substantially parallel to the central axis 22, simultaneously while pivoting and/or rotating of one or both of the end members 24 and 26, and thus the associated endplates. It should be appreciated the the orthopedic implant can 20 achieve three modes of motion: compression, pivoting, and rotation. One or more up to all modes of motion can further be decoupled from one or both of the other modes of motion. For instance, the orthopedic implant 20 can be constructed such that forces that cause the orthopaedic implant 20 to compress do not also cause the orthopaedic implant 20 to pivot or rotate. It is appreciated, however, that the orthopaedic implant 20 is capable of undergoing compression and pivoting and/or rotation simultaneously.

Figure 8:
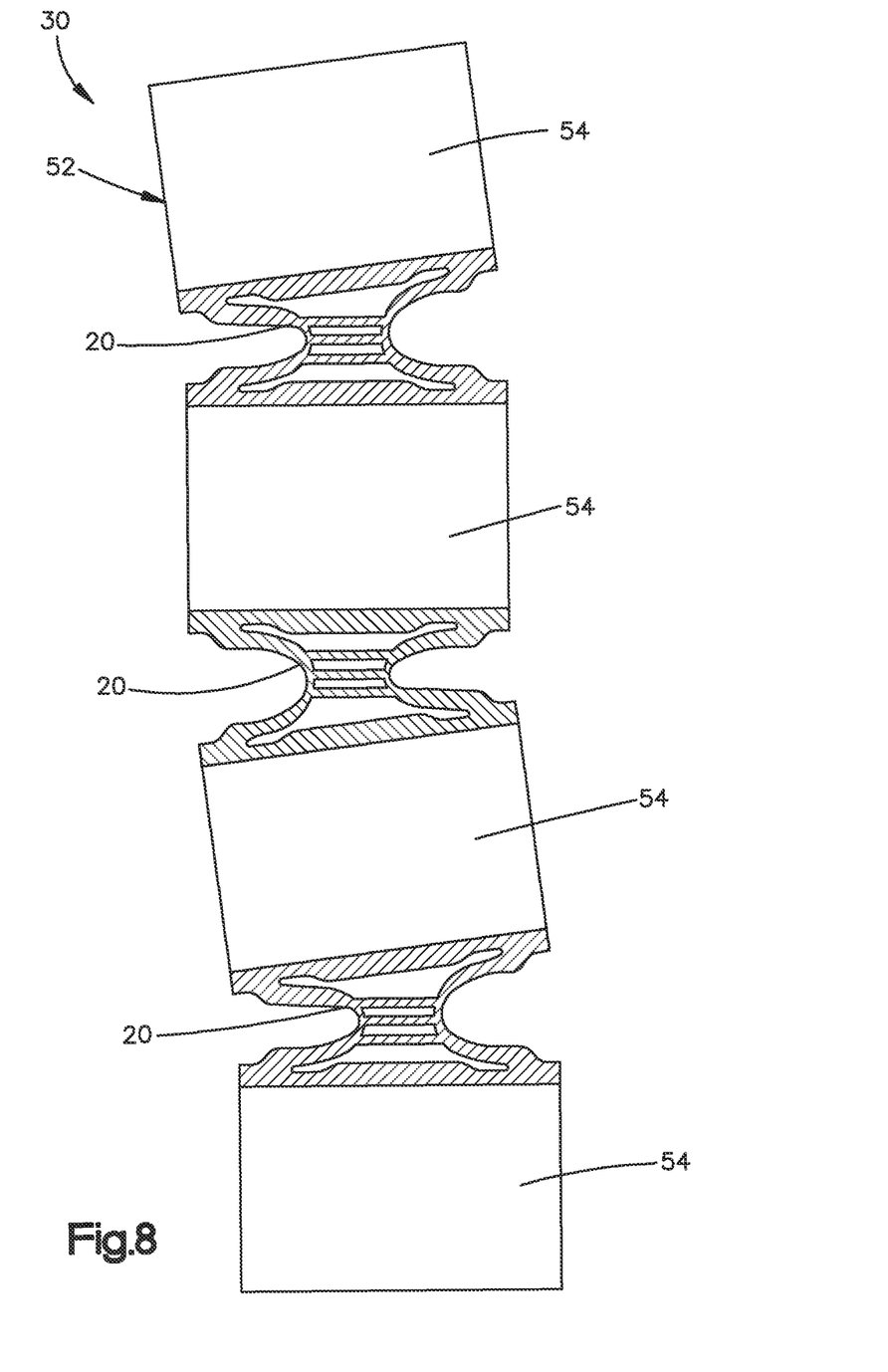
FIG. 8 is a side elevation view of an implant assembly in the form of a flexible rod that includes a plurality of orthopedic implants alternatingly arranged between a plurality of rigid elements.

Referring now to FIG. 8, an implant assembly 30 can be provided as a flexible rod 52 that includes at least a pair, such as a plurality, of substantially rigid bodies 54, and at least one of the orthopaedic implants 20 connected between adjacent ones of the rigid bodies 54. The orthopaedic implants 20 can be constructed in accordance any of the embodiments described herein, and are alternatingly arranged with respect to the rigid bodies 54, such that one of the orthopaedic implants 20 is disposed between a pair of adjacent rigid bodies 54 and a rigid body 54 is disposed between a pair of the orthopaedic implants 20. The rigid bodies 54 can be in the form of vertebral bodies or bones to be operatively coupled via the implant assembly 30, or can be synthetic rigid bodies that are implanted anywhere in the human body as described above.

Figure 9:
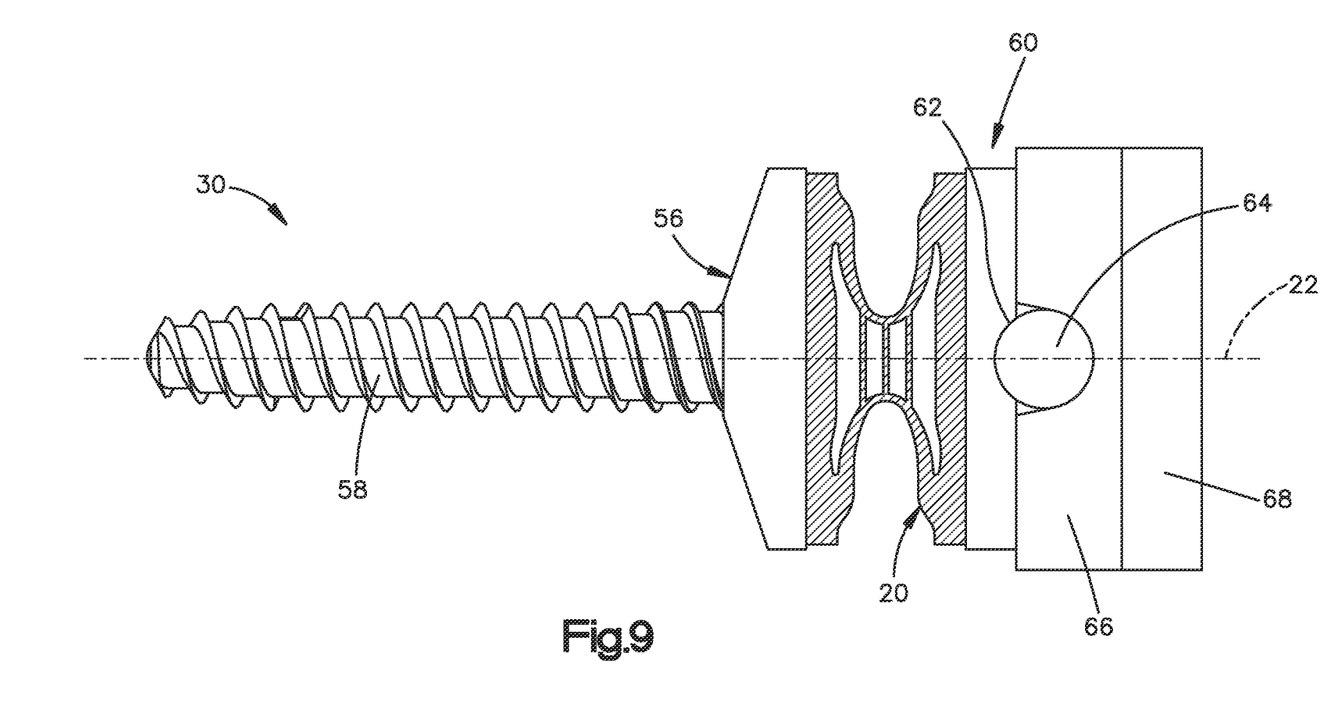
FIG. 9 is a side elevation view of an implant assembly constructed in accordance with an alternative embodiment, including a pedicle screw and an orthopedic implant.

Referring now to FIG. 9, the implant assembly 30 can be provided as a pedicle screw 56 having a shaft 58 and a U-shaped head 60 with a transverse channel 62 that can receive a support rod, such as a spine fixation rod 64 that is connected to at least a pair of pedicle screws, and fix the support rod to the pedicle screw 56. The implant assembly 30 further includes an implant 20 constructed in accordance with any of the embodiments described herein. The implant 20 is disposed in the head 60 at a location between the shaft 58 and the transverse channel 62. The support rod 64 can be fixed in the transverse channel 62 by way of a fixation element 66 and a nut 68 which presses the fixation element 66 onto the support rod 64.

Although various embodiments have been described, it should be understood that changes, substitutions, and alterations can be made herein without departing from the spirit and scope of the invention, for instance as defined by the appended claims. Moreover, the scope of the present application is not intended to be limited to the particular embodiments of the process, machine, manufacture, composition of matter, methods and steps described in the specification. As one of ordinary skill in the art will readily appreciate from the disclosure of the present invention, processes, machines, manufacture, composition of matter, methods, or steps, presently existing or later to be developed that perform substantially the same function or achieve substantially the same result as the corresponding embodiments described herein may be utilized according to the present invention.

The invention claimed is:

1. A compliant orthopaedic implant that is compressible along a central axis, the compliant orthopaedic implant comprising:
   a first member;
   a second member spaced from the first member along the central axis; and
   a compliant interface connected between the first and second members, the compliant interface including at least a pair of spring members that are bracingly connected so as to permit the first and second members to rotate relative to each other about the central axis, wherein each of the at least a pair of spring members space the first member from the second member along the central axis, each spring member of the at least a pair of spring members being curved with respect to the central axis so as to define respective vertices that face each other, wherein application of a compression force to the implant along the central axis causes the spring members to compress, thereby moving the vertices toward the each other along a direction that is angularly offset with respect to the central axis.

2. The compliant orthopaedic implant according to claim 1, wherein at least one bracing is arranged to bracingly connect together the pair of spring members.

3. The compliant orthopaedic implant according to claim 2, wherein the at least one bracing is connected between each of the pair of springs members.

4. The compliant orthopaedic implant according to claim 3, wherein the at least one bracing has a cross-sectional area within the range of approximately 4 mm$^2$ and approximately 6 mm$^2$.

5. The compliant orthopaedic implant according to claim 3, wherein each spring member includes a first end and a second end, the first end of each spring member connected to the first member and the second end of each spring member connected to the second member.

6. The compliant orthopaedic implant according to claim 5, wherein the at least one bracing 1) extends between the first and second spring members along a transverse direction that is perpendicular to the central axis, and 2) is spaced apart from the first and second members along the central axis.

7. The compliant orthopaedic implant according to claim 1, wherein the first member, the second member, and the compliant interface define a single integral structure.

8. The compliant orthopaedic implant according to claim 1, wherein each of the spring members defines an arc with a varying radius of curvature.

9. The compliant orthopaedic implant according to claim 8, wherein the radius of curvature is minimum in the vertex.

10. The compliant orthopaedic implant according to claim 9, wherein the at least one bracing is a transverse bracing that is connected between the vertices of the spring members.

11. The compliant orthopaedic implant according to claim 9, wherein the radius of curvature is within the range of approximately 1 mm and approximately 2 mm.

12. The compliant orthopaedic implant according to claim 1, wherein each spring member extends along a plane that includes the central axis.

13. The compliant orthopaedic implant according to claim 1, wherein the compliant interface includes more than two spring members each defining a plane, and the two planes are angularly equidistantly spaced.

14. The compliant orthopaedic implant according to claim 1, further comprising one or more stops that extending substantially parallel to the central axis between the first and second members.

15. The compliant orthopaedic implant according to claim 14, wherein the stop has a height that is less than the height of the compliant interface in an uncompressed state.

16. The compliant orthopaedic implant according to claim 15, wherein the compliant interface has one or more first contact surfaces and the one or more stops have one or more second contact surfaces suitable to contact the first contact surfaces of the compliant interface when the compliant interface is compressed to the height of one of the stops.

17. The compliant orthopaedic implant according to claim 16, wherein the first and second contact surfaces taper along a direction parallel to the central axis so that the first contact surface can slide on the second contact surface obliquely to the central axis upon asymmetric compression of the compliant orthopaedic implant so as to allow at least one of a lateral translation, a pivotal movement about a pivot axis that is angularly offset with respect to the central axis, and rotation about the central axis of the first and second member relative to each other.

18. The compliant orthopaedic implant according to claim 17, wherein the first and second contact surfaces taper complementarily along the central axis.

19. The compliant orthopaedic implant according to any one of claims 14, wherein the stops are integral with one of the first and second members.

20. The compliant orthopaedic implant according to claim 1, wherein the compliant interface is made from a material that has a modulus of elasticity in the range 10-120 GPa.

21. The compliant orthopaedic implant according to claim 1, wherein the compliant orthopaedic implant has a maximum size greater than 8 mm.

22. The compliant orthopaedic implant according to claim 21, wherein the maximum size is less than 12 cm.

23. The compliant orthopaedic implant according to claim 21, wherein the maximum size is one or more of a length that extends in a first direction substantially transverse to the central axis, a width that extends in a second direction that is substantially transverse to both the first direction and the central axis, and a height that extends substantially along the central axis.

24. The compliant orthopaedic implant according to claim 1, further comprising an artificial joint.

25. The compliant orthopaedic implant according to claim 1, further comprising an artificial intervertebral disc configured to replace a natural intervertebral disc.

26. A compliant orthopaedic implant comprising:
   a first end member defining a first bone engaging surface;
   a second end member defining a second bone engaging surface; and
   a compliant interface including at least a pair of spring members that each extend from the first end member to the second end member such that the first and second end members are spaced apart along a central axis, the at least a pair of spring members being curved with respect to the central axis so as to define respective vertices that face each other, wherein application of a compression force to the implant along the central axis causes the spring members to compress, thereby moving the vertices toward each other, the compliant interface further including at least one stiffening member connected between each of the pair of spring members, the at least one stiffening member configured to permit relative rotation of the first and second end members about the central axis.

27. The compliant orthopaedic implant according to claim 26, wherein the stiffening member is integral with the pair of spring members.

28. The compliant orthopaedic implant according to claim 26, wherein the at least one stiffening member 1) extends from a first spring member of the pair of spring members to second spring member of the pair of springs members along a transverse direction that is perpendicular to the central axis, and 2) is spaced apart from the first and second end members along the central axis.

29. The compliant orthopaedic implant according to claim 26, wherein application of the compression force to the implant along the central axis causes the spring members to compress, thereby moving the vertices toward the each other along a direction that is angularly offset with respect to the central axis.

30. The compliant orthopaedic implant according to claim 26, wherein each of the spring members defines an arc with a varying radius of curvature.

31. The compliant orthopaedic implant according to claim 30, wherein the radius of curvature is minimum in the vertices.

32. The compliant orthopaedic implant according to claim 30, wherein the radius of curvature is within the range of approximately 1 mm and approximately 2 mm.

33. A compliant orthopaedic implant that is compressible along a central axis, the compliant orthopaedic implant comprising:

a first member;
a second member spaced from the first member along the central axis; and
a compliant interface connected between the first and second members, the compliant interface including at least a pair of spring members that are bracingly connected so as to permit the first and second members to rotate relative to each other about the central axis, wherein each of the at least a pair of spring members space the first member from the second member along the central axis, each spring member of the at least a pair of spring members being curved with respect to the central axis so as to define respective vertices that face each other, wherein application of a compression force to the implant along the central axis causes the spring members to compress, thereby moving the vertices toward the central axis along a direction that is angularly offset with respect to the central axis.

34. The compliant orthopaedic implant according to claim 33, the compliant interface further including at least one bracing member connected between each of the pair of spring members, the at least one bracing member configured to permit relative rotation of the first and second end members about the central axis.

35. The compliant orthopaedic implant according to claim 34, wherein the at least bracing member is integral with the pair of spring members.

* * * * *